United States Patent [19]

Butler et al.

[11] Patent Number: 4,525,476
[45] Date of Patent: Jun. 25, 1985

[54] N-[1-OXO-3-(5-OXO-2-PYRROLIDINYL)-PROPYL]-ALPHA-AMINOACIDS AND DERIVATIVES AS COGNITION ACTIVATORS

[75] Inventors: Donald E. Butler; Fred M. Hershenson; Michael R. Pavia, all of Ann Arbor, Mich.

[73] Assignee: Warner-Lambert Company, Morris Plains, N.J.

[21] Appl. No.: 498,449

[22] Filed: May 26, 1983

[51] Int. Cl.$^3$ .................. C07D 403/06; C07D 401/06; C07D 207/09; A61K 31/40
[52] U.S. Cl. .................................... 514/326; 514/422; 514/414; 548/465; 548/467; 548/518; 548/550; 546/208
[58] Field of Search ............... 548/518, 550, 465, 467; 424/274, 267; 546/208

[56] References Cited

U.S. PATENT DOCUMENTS

| | | | |
|---|---|---|---|
| 3,459,738 | 8/1969 | Morren et al. | 424/274 |
| 4,144,246 | 3/1979 | L'Italien et al. | 424/274 |
| 4,145,347 | 3/1979 | L'Italien et al. | 544/372 |
| 4,372,966 | 2/1983 | Butler | 424/274 |

OTHER PUBLICATIONS

Colonge et al., Bul. Soc. Chim. France, vol. 3, (1962), pp. 598–603.
Leonard et al., J. Am. Chem. Soc., vol. 69, (1947), pp. 690–692.

Primary Examiner—Donald G. Daus
Assistant Examiner—W. A. Teoli, Jr.
Attorney, Agent, or Firm—Jerry F. Janssen

[57] ABSTRACT

N-[1-oxo-3-(5-oxo-2-pyrrolidinyl)propyl]-alpha-aminoacids, base addition salts, esters, and amides are useful as cognition activators. Pharmaceutical compositions containing these compounds and methods of using the pharmaceutical compositions for treating senility or amnesia are also disclosed.

21 Claims, No Drawings

N-[1-OXO-3-(5-OXO-2-PYRROLIDINYL)PROPYL]-ALPHA-AMINOACIDS AND DERIVATIVES AS COGNITION ACTIVATORS

BACKGROUND OF THE INVENTION

The present invention relates to chemical compounds and pharmaceutical compositions useful as cognition activators. More particularly, this invention concerns N-[1-oxo-3-(5-oxo-2-pyrrolidinyl)propyl]-alpha-aminoacids, their salts, esters, and amides, pharmaceutical compositions employing such compounds, and a method of treating senility or reversing amnesia in mammals caused by electroconvulsive shock by employing such pharmaceutical compositions.

5-Oxo-2-pyrrolidinepropanoic acid amide, then known as pyrrolidin-2-one-5-propanoic acid amide, was synthesized as a solid derivative in the characterization of gamma-chloropimelic acid dimethyl ester as reported by H. Leuchs and W. Nagel, Chem. Ber., 55B, 3950-3960 (1922). The propanoic acid amide was also obtained by hydrogenation of an ammonia derivative of gamma-ketopimelic acid diethyl ester by A. Scipioni, Ann Chim. (Rome), 42, 53-61 (1952). The propanoic acid amide is also mentioned in Italian Pat. No. 482,946 as an intermediate in the synthesis of gamma-aminopimelic acid.

The piperidide of 5-oxo-2-pyrrolidinepropanoic acid is reported by F. Michael and H. Albers, Ann., 581, 225-237 (1953) as a crystalline derivative from 3,5-dioxopyrrolizidine.

SUMMARY OF THE INVENTION

There is provided, in accordance with a first aspect of the present invention, a compound having the structural formula I:

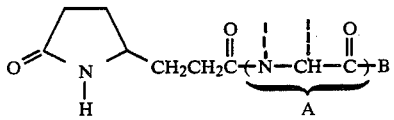

wherein A is an alpha-aminoacid residue, and B is hydroxy, alkoxy of from one to six carbon atoms, haloalkoxy of from two to six carbon atoms where the haloatom is attached to carbon 2 to 6 of the haloalkoxy group, $-NR_1R_2$ where $R_1$ and $R_2$ are independently hydrogen or alkyl of from one to six carbon atoms, or $-OR_3$ where $R_3$ is a pharmaceutically acceptable cation.

In accordance with a second aspect, the present invention provides a method of preparing a compound having structural formula I by reacting dihydro-1H-pyrrolizine-3,5(2H,6H)-dione with the 1,1-dimethylethyl or benzyl ester of an alpha-aminoacid. The resulting esters are subsequently converted to the corresponding free acids, salts, or amides, if desired, by conventional techniques.

In accordance with a third aspect of the present invention, a method of preparing compounds of the structural formula I where B is alkoxy comprises converting compounds of formula I where B is 1,1-dimethylethoxy by ester interchange reactions.

In accordance with a fourth aspect of the present invention, an alternative method of preparing compounds of the structural formula I is provided wherein 5-oxo-2-pyrrolidinepropanoic acid is reacted with a compound having structural formula II:

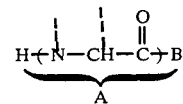

wherein A is an alpha-aminoacid residue, and B is hydroxy, alkoxy of from one to six carbon atoms, haloalkoxy of from two to six carbon atoms where the haloatom is attached to carbon 2 to 6 of the haloalkoxy group, or $-NR_1R_2$ where $R_1$ and $R_2$ are independently hydrogen or alkyl of from one to six carbon atoms. The free acids are converted to compounds of formula I wherein B is $OR_3$ and $R_3$ is a pharmaceutically acceptable cation, if desired, by conventional techniques.

In accordance with a fifth aspect of the present invention, there are provided pharmaceutical compositions comprising an effective amount of a compound having structural formula I, wherein A and B are as defined above, in combination with a pharmaceutically acceptable carrier.

In accordance with a sixth aspect of the present invention, a method of treating senility or reversing amnesia caused by electroconvulsive shock in a mammal in need of such treatment comprises administering to the mammal a pharmaceutical composition as defined above.

DETAILED DESCRIPTION

Compounds falling within the scope of this invention are 5-oxo-2-pyrrolidin-2-propanoyl-alpha amino acids, their esters, amides, and pharmaceutically acceptable salts, particularly the L-aminoacid derivatives of 5-oxo-2-pyrrolidin-2-propanoic acid. As used throughout this specification and the appended claims, the term "alpha-aminoacid residue" means the chemical grouping consisting of the nitrogen atom, alpha carbon atom, and acyl group of an alpha-aminoacid, and the attached hydrogen, or alpha carbon side-chain aliphatic, alicyclic, aromatic, heterocyclic or heteroaromatic groups including polymethylene linkages forming closed rings between the alpha-carbon atom and nitrogen atom. The unsatisfied valence bonds indicated by the dotted lines in structural formula I above are to be understood as being satisfied by attachment to hydrogen, the alpha carbon side chain group, or a polymethylene linkage between the nitrogen and alpha carbon atoms. L-Alpha-aminoacids providing the aminoacid residues of compounds of this invention are selected from the alpha-aminoacids having neutral or uncharged side-chain groups attached to the alpha-carbon atom including alanine, valine, leucine, isoleucine, phenylalanine, tryptophan, methionine, glycine, serine, threonine, cysteine, tyrosine, asparagine, and glutamine as well as alpha-aminoacids in which the alpha-carbon atom and nitrogen atom are linked through a polymethylene chain forming a ring, such as proline, pipecolic acid, and the like.

The alkyl groups contemplated by the invention, unless otherwise stated, comprise both straight carbon chain and branched carbon chain groups of from one to about six carbon atoms. By the term "haloalkoxy" group is meant an alkyl group thus defined, attached through an oxygen atom and substituted with one or more atoms selected from fluorine, chlorine, bromine, or iodine at a position at least two carbon atoms from the oxygen atom of the alkoxy group.

Compounds of the present invention can exist in the unsolvated as well as solvated forms, including hydrated forms. In general, the forms solvated with pharmaceutically acceptable solvents such as water, ethanol, and the like, are equivalent to the unsolvated forms for the purposes of this invention.

The compounds of this invention contain at least two potentially asymmetric carbon atoms, one at the 2-position of the 5-oxo-2-pyrrolidinepropanoic acid sub-unit and at least one in the aminoacid residue at the alpha-carbon atom, both indicated by asterisks in the structural formula below:

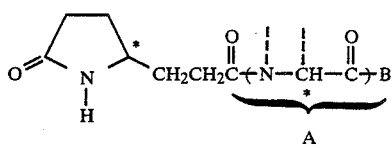

The invention contemplates compounds in which the stereochemistry at the 2-position of the 5-oxo-2-pyrrolidinepropanoic acid sub-unit is substantially entirely S, substantially entirely R, or various mixtures thereof. Further, in its broadest aspect, the invention also contemplates both D- and L-alpha-aminoacid residues, including mixtures thereof. In a sub-generic aspect, the invention contemplates L-alpha-aminoacid residues. The compounds contemplated by the present invention may thus comprise compounds having any of the above combinations of stereochemistry at the 2-position of the 5-oxo-2-pyrrolidinepropanoic acid sub-unit and the alpha-aminoacid residue.

In a first embodiment, a compound of the present invention has the name N-[1-oxo-3-(5-oxo-2-pyrrolidinyl)propyl]-L-leucine, 1,1-dimethylethyl ester.

In another embodiment, a compound of this invention has the name N-[1-oxo-3-(5-oxo-2-pyrrolidinyl) propyl]-L-alanine.

In a further embodiment, a compound of the present invention has the name N-[1-oxo-3-(5-oxo-2-pyrrolidinyl)propyl]-L-alanine, ethyl ester.

In another embodiment, a compound of the present invention has the name N-[1-oxo-3-(5-oxo-2-pyrrolidinyl)propyl]-L-alanine, 1,1-dimethylethyl ester.

In still another embodiment, a compound of the present invention has the name N-[1-oxo-3-(5-oxo-2-pyrrolidinyl)propyl]-L-alanine, 4-chlorobutyl ester.

In another embodiment, a compound of this invention has the name N-[1-oxo-3-(5-oxo-2-pyrrolidinyl)propyl]-L-methionine, methyl ester.

In yet another embodiment, a compound of the present invention has the name N-[1-oxo-3-(5-oxo-2-pyrrolidinyl)propyl]-L-phenylalanine, methyl ester.

In another embodiment, a compound of the present invention has the name 1-[1-oxo-3-(5-oxo-2-pyrrolidinyl)propyl]-L-proline, methyl ester.

In another embodiment, a compound of the present invention has the name 1-[1-oxo-3-(5-oxo-2-pyrrolidinyl)propyl]-2-pyrrolidinecarboxamide[2S].

Compounds of the present invention are prepared by standard methods. One general method involves the reaction of dihydro-1H-pyrrolizine-3,5(2H,6H)-dione with an alpha-aminoacid esterified with, for example, 1,1-dimethylethanol or benzyl alcohol. Dihydro-1H-pyrrolizine-3,5(2H,6H)-dione, also known as 3,5-dioxopyrrolizidine and as 1-aza-bicyclo[3.3.0]octane, is prepared by the method detailed in U.S. Pat. No. 4,372,966.

The mixture of dihydro-1H-pyrrolizine-3,5(2H,6H)-dione and the esterified amino acid is heated in a polar inert solvent, such as acetonitrile, or without solvent at a temperature of between about 25° C. to about 150° C. Sufficient time should be allowed for complete reaction to permit easier purification of the end product. Reaction times of between about 1 to 96 hours are sufficient, with longer reaction times required at lower temperatures.

If desired, the resulting 1,1-dimethylethyl esters are converted to the corresponding substituted alpha-aminoacids by standard acidic tert-butyl cleavage. The benzyl esters are converted to the corresponding substituted alpha-aminoacids by catalyzed hydrogenolysis. The free substituted aminoacids are converted, if desired, to the corresponding salts, esters, or amides by well known methods.

The 1,1-dimethylethyl or benzyl esters may be converted to other esters by transesterification reaction, or other esters may be prepared by direct esterification of the free aminoacid derivatives.

Alternatively, compounds of the present invention may be synthesized by reacting 5-oxo-2-pyrrolidinepropanoic acid with a compound of the general structural formula II where A is an alpha-aminoacid residue and B is hydroxy, alkoxy of from one to six carbon atoms, or —NR₁R₂ where R₁ and R₂ are independently selected from hydrogen or alkyl of from one to six carbon atoms.

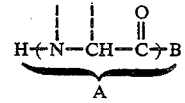

The synthesis of the acid is reported in Coll. Czech. Chem. Comm., 12, 278 (1947). Compounds of general formula II are synthesized from the appropriate aminoacids by techniques generally known to those skilled in the art.

The coupling of 5-oxo-2-pyrrolidinepropanoic acid and the alpha-aminoacid derivative II is aided by the use of a soluble carbodiimide such as dicyclohexylcarbodiimide and a catalyst such as 4-dimethylaminopyridine. The reaction is carried out in the cold at temperatures between 0° C. (or lower) and 25° C. in an aprotic solvent such as dichloromethane, acetonitrile, tetrahydrofuran, diethyl ether, and the like.

The compounds of the present invention (structure I) in which B comprises hydroxyl form pharmaceutically acceptable salts with organic and inorganic bases. Examples of suitable inorganic bases are ammonium hydroxide, sodium hydroxide, potassium hydroxide, sodium carbonate, calcium carbonate, sodium bicarbonate, and the like. Pharmaceutically acceptable salts are also formed with amine cations derived from organic nitrogenous bases strong enough to form cations.

The pharmaceutically-acceptable salts of the acid are prepared by for example, suspending the acid in water and adjusting the pH with the pharmaceutically-acceptable base, or by reacting the compound of formula I, where B is hydroxyl with one equivalent of the pharmaceutically acceptable base in a solvent and removing the solvent under reduced pressure.

The term, pharmaceutically acceptable metal cation contemplates the positively charged ions derived from such metals as sodium, potassium, calcium, magnesium, aluminum, zinc, iron, and the like. The salts are prepared by contacting the free form of the compound with an equivalent amount of the desired base in the conventional manner. The free forms may be regenerated by treating the salt form with an acid. For example, dilute aqueous acid solutions may be utilized to regenerate the free form from a respective salt. Dilute aqueous hydrochloric acid is suitable for this purpose. The free forms differ from their respective salt forms somewhat in certain physical properties such as solubility in polar solvents, but the salts are otherwise equivalent to their respective free base forms for purposes of the invention.

The term pharmaceutically acceptable amine cation contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

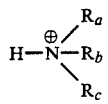

wherein $R_a$, $R_b$, and $R_c$, independently, are hydrogen, alkyl of from about one to about six carbon atoms, cycloalkyl of from about three to about six carbon atoms, aryl of about six carbon atoms, aralkyl of from about 7 to about 11 carbon atoms, hydroxyalkyl of from about 2 to about 4 carbon atoms, or monoarylhydroxyalkyl of from about 8 to about 15 carbon atoms, or, when taken together with the nitrogen atom to which they are attached, any two of $R_a$, $R_b$, and $R_c$ may form part of a 5 to 6-membered heterocyclic ring containing carbon, hydrogen, oxygen, or nitrogen, said heterocyclic rings and said aryl groups being unsubstituted or mono- or dialkyl substituted said alkyl groups containing from about one to about six carbon atoms. Illustrative therefore of $R_a$, $R_b$, and $R_c$ groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di-, and triethanolammonium, ethyldiethanolammonium, n-butylmonoethanolammonium, tris(hydroxymethyl)-methylammonium, phenylmonoethanolammonium, and the like.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatable therapeutic agents.

In therapeutic use as cognition activators, the mammalian dosage range for a 70 kg subject is from 1 to 1500 mg/kg of body weight per day or preferably 25 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The effectiveness of the aforementioned compounds was determined by the test designed to show the compound's ability to reverse amnesia produced by electroconvulsive shock. The test is fully described in U.S. Pat. No. 4,145,347, issued Mar. 20, 1979, and is herein incorporated by reference. The test compounds in the present instance were administered orally, and the duration of the electroconvulsive shock was 1.0 seconds.

The following criteria are used in interpreting the percent of amnesia reversal scores: 40 percent or more (active=A) 25 to 39 percent (borderline=C) and 0 to 24 percent (inactive=N).

The table below reports the percent of amnesia reversal of examples of orally administered compounds of the present invention.

TABLE

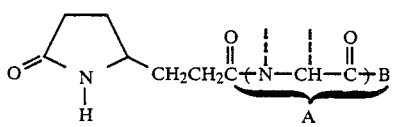

| Amino Acid Residue | | Administered Dose (mg/kg Body Wt) | | |
|---|---|---|---|---|
| A | B | 100 | 10 | 1 |
| Leucyl | —OC(CH$_3$)$_3$ | 41 (A) | 41 (A) | 29 (C) |
| Leucyl | —OCH$_3$ | 74 (A) | 74 (A) | 48 (A) |
| Alanyl | —OC(CH$_3$)$_3$ | 100 (A) | 44 (A) | 22 (N) |
| Alanyl | —OCH$_2$CH$_3$ | 46 (A) | 38 (C) | 77 (A) |
| Alanyl | —O(CH$_2$)$_4$Cl | 94 (A) | 80 (A) | 88 (A) |
| Methionyl | —OCH$_3$ | 60 (A) | 26 (C) | 70 (A) |
| Phenylalanyl | —OCH$_3$ | 80 (A) | 53 (A) | 33 (C) |
| Prolyl | —OCH$_3$ | 54 (A) | 74 (A) | 54 (A) |
| Prolyl | —NH$_2$ | 27 (C) | 24 (N) | 0 (N) |

The following examples are provided to permit one skilled in the art to practice the present invention. However, the examples are merely illustrative of the invention, and should not be construed as limiting the scope of the invention as defined by the appended claims.

Chemical Compositions

EXAMPLE 1

Preparation of N-[1-oxo-3-(5-oxo-2-pyrrolidinyl)propyl]-L-leucine, 1,1-dimethylethyl ester A solution of 7.0 g (0.05 mol) of dihydro-1H-3,5(2H,6H)dioxopyrrolizidine in 150 ml of acetonitrile is treated with 14.05 g (0.075 mol) L-Leucine 1,1-dimethylethyl ester. The mixture is refluxed 24 hours. The solution is concentrated under reduced pressure and the resulting oil is chromatographed over silica gel using elution with 2.5% methanol in dichloromethane. After concentration at reduced pressure, the oil is rechromatographed over silica gel using 19:1 dichloromethane:methanol. The eluate is concentrated at reduced pressure and heated at 80° C. to yield N-[1-oxo-3-(5-oxo-2-pyrrolidinyl)-propyl]-L-leucine, 1,1-dimethylethyl ester as an analytically pure oil with the following characteristic proton NMR spectrum: 1H-NMR(CDCL3) 0.92(d, 6H), 1.42 (s, 9H), 1.4–1.9 (m, 5H), 2.2–2.4 (m, 7H), 3.5–3.8 (m, 1H), 4.2–4.5 (m, 1H), 6.25–6.5 (m, 1H).

EXAMPLE 2

Preparation of N-[1-oxo-3-(5-oxo-2-pyrrolidinyl)propyl]-L-alanine, 1,1-dimethylethyl ester A solution of 7.0 g (0.05 mol) of dihydro-1H-3,5(2H,6H) dioxopyrrolizidine in 150 ml of acetonitrile is treated with 14.5 g (0.1 mol) L-alanine 1,1-dimethylethyl ester. The mixture is refluxed 24 hours. The solution is concentrated at reduced pressure and the resulting oil is chromatographed over silica gel using elution with 2.5% methanol in dichloromethane. After concentration at reduced pressure the oil is rechromatographed over silica gel using 19:1 dichloromethane:methanol. The eluate is concentrated at reduced pressure and heated at 80° C. to yield N-[1-oxo-3-(5-oxo-2-pyrrolidinyl)propyl]-L-alanine, 1,1-dimethylethyl ester as an analytically pure oil with the following characteristic proton NMR spectrum: 1H-NMR(CDCL3) 1.35 (d, 3H), 1.5 (s, 9H), 1.5–2.4 (m, 9H), 3.5–3.8 (m, 1H), 4.4 (m, 1H), 6.6–6.8 (m, 1H), 7.4–7.6 (m, 1H).

EXAMPLE 3

Preparation of N-[1-oxo-3-(5-oxo-2-pyrrolidinyl) propyl]-L-leucine, methyl ester A solution of 3.0 g (0.017 mol) L-Leucine methyl ester hydrochloride is dissolved in 30 ml of dichloromethane. The solution is cooled to 0° C. and 4.05 ml (0.029 mol) of triethylamine is added dropwise over a ten minute period. The mixture is stirred ten minutes, filtered and concentrated at reduced pressure. The oil is dissolved in 17 ml of dichloromethane and the following is added in a single addition: 4.35 g (0.021 mol) of dicyclohexylcarbodiimide; 100 mg (0.0008 mol) of 4-dimethylaminopyridine; 2.66 g (0.017 mol) of 5-oxo-2-pyrrolidinepropanoic acid. The reaction is allowed to warm to room temperature and stirred for 20 hours. The solids are removed by filtration and are washed with 15 ml of 0° C. dichloromethane. The filtrate is concentrated at reduced pressure to an oil. The oil is chromatographed over silica gel using 93:7 dichloromethanemethanol for elution. Concentration at reduced pressure followed by heating at 0.1 mm pressure and 50° C. yields crystalline analytically pure (as a 0.33 hydrate) N-[1-oxo-3-(5-oxo-2-pyrrolidinyl) propyl]-L-leucine, methyl ester with a melting point of 70°–74.5° C.

EXAMPLE 4

Preparation of N-[1-oxo-3-(5-oxo-2-pyrrolidinyl)propyl]-L-methionine, methyl ester A solution of 5.0 g (0.025 mol) L-methionine methyl ester hydrochloride is dissolved in 30 ml of dichloromethane. The solution is cooled to 0° C. and 4.42 ml (0.028 mol) of triethylamine is added dropwise over a ten minute period. The mixture is stirred 15 minutes, filtered, and a mixture of the following is added in a single addition: 6.32 g (0.03 mol) of dicyclohexylcarbodiimide; 200 mg (0.0016 mol) of 4-dimethylaminopyridine; 3.85 g (0.025 mol) of 5-oxo-2-pyrrolidinepropanoic acid. The reaction is allowed to warm to room temperature and stirred for 24 hours. The solids are removed by filtration and are washed with 15 ml of 0° C. dichloromethane. The filtrate is concentrated at reduced pressure to an oil. The oil is chromatographed over silica gel using 19:1 dichloromethanemethanol for elution. Concentration at reduced pressure followed by heating at 0.1 mm pressure and 60° C. yields crystalline analytically pure N-[1-oxo-3-(5-oxo-2-pyrrolidinyl)-propyl]-L-methionine, methyl ester with a melting point of 98°–100° C.

EXAMPLE 5

Preparation of N-[1-oxo-3-(5-oxo-2-pyrrolidinyl)propyl]-L-alanine, 4-chlorobutyl ester A solution of 4.0 g (0.014 mol of L-alanine, N-[1-oxo-3-(5-oxo-2-pyrrolidinyl)propyl]-, 1,1-dimethylethyl ester in 40 ml of tetrahydrofuran is cooled to 0° C. and 10 ml of a 3% solution of hydrogen chloride in tetrahydrofuran is added over five minutes. The reaction is allowed to warm to room temperature and is stirred for 24 hours. The mixture is heated at 45°–50° C. for 24 hours. The mixture is cooled and concentrated at reduced pressure to yield an oil. The oil is chromatographed over silica gel using 19:1 methylene chloride:methanol for elution. After concentration at reduced pressure the pure oil crystallizes to yield N-[1-oxo-3-(5-oxo-2-pyrrolidinyl-propyl]-L-alanine, 4-chlorobutyl ester with a melting point of 86°–87° C.

EXAMPLE 6

Preparation of N-[1-oxo-3-(5-oxo-2-pyrrolidinyl) propyl]-L-alanine, ethyl ester

A solution of 5.0 g (0.033 mol) L-alanine ethyl ester hydrochloride is dissolved in 30 ml of dichloromethane. The solution is cooled to 0° C. and 5.42 ml (0.039 mol) of triethylamine is added dropwise over a ten minute period. The mixture is stirred 15 minutes, filtered, concentrated, and diluted with 60 ml of dichloromethane. A mixture of the following is added in a single addition: 4.84 g (0.025 mol) of dicyclohexylcarbodiimide; 200 mg (0.0016 mol) of 4-dimethylaminopyridine; 3.08 g (0.02 mol) of 5-oxo-2-pyrrolidinepropanoic acid. The reaction is allowed to warm to room temperature and stirred for 24 hours. The solids are removed by filtration and are washed with 15 ml of 0° C. dichloromethane. The filtrate is concentrated at reduced pressure to an oil. The oil is chromatographed over silica gel using 19:1 dichloromethane-methanol for elution. Concentration at reduced pressure followed by heating at 0.1 mm pressure and 60° C. yields crystalline analytically pure N-[1-oxo-3-(5-oxo-2-pyrrolidinyl)propyl]-L-alanine, ethyl ester with a melting point of 88°–90° C.

EXAMPLE 7

Preparation of N-[1-oxo-3-(5-oxo-2-pyrrolidinyl)propyl]-L-phenylalanine, methyl ester A solution of 6.0 g (0.028 mol) L-phenylalanine methyl ester hydrochloride is dissolved in 30 ml of dichloromethane. The solution is cooled to 0° C. and 4.65 ml (0.033 mol) of triethylamine is added dropwise over a 10 minute period. The mixture is stirred 15 minutes, filtered, concentrated, and diluted with 70 ml of dichloromethane. At 0° C., a mixture of the following is added in a single addition: 6.87 g (0.033 mol) of dicyclohexylcarbodiimide; 200 mg (0.0016 mol) of 4-dimethylaminopyridine; 4.4 g (0.028 mol) of 5-oxo-2-pyrrolidinepropanoic acid. The reaction is allowed to warm to room temperature and stirred for 24 hours. The solids are removed by filtration and are washed with 15 ml of 0° C. dichloromethane. The filtrate is concentrated at reduced pressure to an oil.

The oil is chromatographed over silica gel using 19:1 dichloromethane-methanol for elution. Concentration at reduced pressure followed by heating at 0.1 mm pressure and 60° C. yields analytically pure (as the 0.45 hydrate) N-[1-oxo-3-(5-oxo-2-pyrrolidinyl)propyl]-L-phenylalanine, methyl ester as an oil with the following characteristic proton NMR spectrum: 1H-NMR (CDCL3) 1.4–2.4 (m, 8H), 2.8–3.3 (m, 3H), 3.72 (s, 3H), 4.7–5.0 (m, 1H), 6.9 (m, 1H) 7.2 (m, 5H), 7.65 (m, 1H).

EXAMPLE 8

Preparation of 1-[1-oxo-3-(5-oxo-2-pyrrolidinyl)propyl]-L-proline, methyl ester

A solution of 5.0 g (0.03 mol) L-proline methyl ester hydrochloride is dissolved in 30 ml of dichloromethane. The solution is cooled to 0° C. and 4.42 ml (0.032 mol) triethylamine is added dropwise over a ten minute period. The mixture is stirred 15 minutes and a mixture of the following is added in a single addition: 6.85 g (0.033 mol) of dicyclohexylcarbodiimide; 200 mg (0.0016 mol) of 4-dimethylaminopyridine; 4.71 g (0.03 mol) of 5-oxo-2-pyrrolidinepropanoic acid. The reaction is allowed to warm to room temperature and stirred for 24 hours. The solids are removed by filtration and are washed with 15 ml of 0° C. dichloromethane. The filtrate is concentrated at reduced pressure to an oil. The oil is chromatographed over silica gel using 12:1 dichloromethanemethanol for elution. Concentration at reduced pressure followed by heating at 0.1 mm pressure and 60° C. yields 1-[1-oxo-3-(5-oxo-2-pyrrolidinyl)propyl]-L-proline, methyl ester as an analytically pure oil (0.55 hydrate) with the following characteristic proton NMR spectrum: 1H-NMR (CDCL3) 1.6–2.5 (m, 14H), 3.4–3.85 (m, 2H), 3. (s, 3H), 4.5 (m, 1H), 6.37 (m, 1H).

EXAMPLE 9

Preparation of 1-[1-oxo-3-(5-oxo-2-pyrrolidinyl)propyl]-2-pyrrolidinecarboxamide[2S]

A solution of 5.0 g (0.033 mol) L-prolinamide hydrochloride is dissolved in 30 ml of dichloromethane. The solution is cooled to 0° C. and 5.1 ml (0.037 mol) of triethylamine is added dropwise over a ten minute period. The mixture is stirred 15 minutes, filtered, and concentrated, and diluted with 25 ml of dichloromethane. A mixture of the following is added in a single addition 5.0 g (0.024 mol) of dicyclohexylcarbodiimide; 200 mg (0.0016 mol) of 4-dimethylaminopyridine; 3.44 g (0.022 mol) of 5-oxo-2-pyrrolidinepropanoic acid. The reaction is allowed to warm to room temperature and stirred for 24 hours. The solids are removed by filtration and are washed with 15 ml of 0° C. dichloromethane. The filtrate is concentrated at reduced pressure to an oil. The oil is chromatographed over silica gel using 4:1 dichloromethane-methanol for elution. Concentration at reduced pressure followed by heating at 0.1 mm pressure and 60° C. yields an analytically pure oil (as a 1.45 hydrate) of 1-[1-oxo-3-(5-oxo-2-pyrrolidinyl)-propyl]-2-pyrrolidinecarboxamide[2S] with the following characteristic proton NMR spectrum: 1H-NMR (CDCL3) 1.6–2.6 (m, 12H), 3.4–3.9 (m, 3H), 4.5 (m, 1H), 6.15 (m, 1H) 7.0–7.8 (m, 2H).

EXAMPLE 10

Preparation of N-[1-oxo-3-(5-oxo-2-pyrrolidinyl) propyl]-L-alanine

Seven hundred and twenty milligrams (0.00243 mol) of L-alanine, N-[1-oxo-3-(5-oxo-2-pyrrolidinyl)propyl]-, 1,1-dimethylethyl ester are added to 5 ml of trifluoroacetic acid at 0° C. The solution is stirred and heated at 50° C. for ten minutes. The trifluoroacetic acid is removed at reduced pressure and heptane is used to remove the last traces by addition and reconcentration at reduced pressure. Ethyl acetate, 100 ml, is added to the residue and the mixture is heated to reflux. The residual oil crystallizes. The crystalline N-[1-oxo-3-(5-oxo-2-pyrrolidinyl)propyl]-L-alanine is isolated by filtration, and after drying at 25° C. and 0.1 mm has a melting point of 174°–179° C.

We claim:

1. A compound having the structural formula

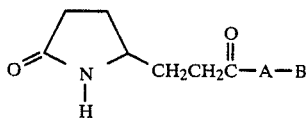

wherein A is a divalent alpha-aminoacid group selected from alanine, valine, leucine, isoleucine, phenylalanine, tryptophan, methionine, glycine, serine, threonine, cysteine, tyrosine, asparagine, glutamine, proline, and pipecolic acid, and B is hydroxy, alkoxy of from one to six carbon atoms, haloalkoxy of from two to six carbon atoms where the halo-atom is attached to carbon two to six of the haloalkoxy group, $-NR_1R_2$ where $R_1$ and $R_2$ are independently hydrogen or alkyl of from one to six carbon atoms, or $-OR_3$ where $R_3$ is a pharmaceutically acceptable cation.

2. The compound defined in claim 1 wherein said divalent alpha-aminoacid group is derived from an L-alpha-aminoacid.

3. The compound defined in claim 1 having the name N-[1-oxo-3-(5-oxo-2-pyrrolidinyl)propyl]-L-leucine, 1,1-dimethylethyl ester.

4. The compound defined in claim 1 having the name N-[1-oxo-3-(5-oxo-2-pyrrolidinyl)propyl]-L-alanine.

5. The compound defined in claim 1 having the name N-[1-oxo-3-(5-oxo-2-pyrrolidinyl)propyl]-L-alanine, ethyl ester.

6. The compound defined in claim 1 having the name N-[1-oxo-3-(5-oxo-2-pyrrolidinyl)propyl]-L-alanine, 1,1-dimethylethyl ester.

7. The compound defined in claim 1 having the name N-[1-oxo-3-(5-oxo-2-pyrrolidinyl)propyl]-L-alanine, 4-chlorobutyl ester.

8. The compound defined in claim 1 having the name N-[1-oxo-3-(5-oxo-2-pyrrolidinyl)propyl]-L-methionine, methyl ester.

9. The compound defined in claim 1 having the name N-[1-oxo-3-(5-oxo-2-pyrrolidinyl)propyl]-L-phenylalanine, methyl ester.

10. The compound defined in claim 1 having the name 1-[1-oxo-3-(5-oxo-2-pyrrolidinyl)propyl]-L-proline, methyl ester.

11. The compound defined in claim 1 having the name 1-[1-oxo-3-(5-oxo-2-pyrrolidinyl)propyl]-2-pyrrolidinecarboxamide[2S].

12. A pharmaceutical composition comprising an amount of a compound having the structural formula

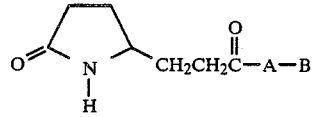

effective for treating senility, wherein A is a divalent alpha-aminoacid group selected from alanine, valine, leucine, isoleucine, phenylalanine, tryptophan, methionine, glycine, serine, threonine, cysteine, tyrosine, asparagine, glutamine, proline, and pipecolic acid, and B is hydroxy, alkoxy of from one to six carbon atoms, haloalkoxy of from two to six carbon atoms where the halo-atom is attached to carbon two to six of the haloalkoxy group, $-NR_1R_2$ where $R_1$ and $R_2$ are independently hydrogen or alkyl of from one to six carbon atoms, or $-OR_3$ where $R_3$ is a pharmaceutically acceptable cation, in combination with a pharmaceutically acceptable carrier.

13. The pharmaceutical composition defined in claim 12 wherein said divalent alpha-aminoacid group is derived from an L-alpha-aminoacid.

14. The pharmaceutical composition defined in claim 12 wherein said composition is in the form of a solid.

15. The pharmaceutical composition defined in claim 12 wherein said composition is in the form of a liquid.

16. The pharmaceutical composition defined in claim 12 wherein said solid is converted to a liquid form such as a solution, suspension, or emulsion before use.

17. The pharmaceutical composition defined in claim 12 which is a liquid intended for oral use.

18. The pharmaceutical composition defined in claim 16 which is intended for oral use.

19. The pharmaceutical composition defined in claim 12 which is a liquid intended for parenteral use.

20. The pharmaceutical composition defined in claim 16 which is intended for parenteral use.

21. A method for treating senility or for reversing amnesia caused by electroconvulsive shock in a mammal in need of said treatment, which method comprises administering to said mammal the pharmaceutical composition defined in claim 12.

* * * * *